(12) United States Patent
Xu et al.

(10) Patent No.: US 8,680,993 B2
(45) Date of Patent: Mar. 25, 2014

(54) SYSTEM AND APPARATUS FOR GLOSS CORRECTION IN COLOR MEASUREMENTS

(75) Inventors: Zhiling Xu, Princeton Junction, NJ (US); Taeyoung Park, Princeton, NJ (US)

(73) Assignee: Datacolor Holding AG, Lucerne (CH)

( * ) Notice: Subject to any disclaimer, the term of this patent is extended or adjusted under 35 U.S.C. 154(b) by 264 days.

(21) Appl. No.: 13/327,072

(22) Filed: Dec. 15, 2011

(65) Prior Publication Data
US 2013/0154830 A1    Jun. 20, 2013

(51) Int. Cl.
*G08B 21/00* (2006.01)
(52) U.S. Cl.
USPC .............................. 340/540; 356/421; 356/448
(58) Field of Classification Search
USPC .......... 340/540, 555–557, 619; 382/162, 209;
250/559.1; 356/73, 328, 405, 419, 421,
356/445, 448, 600; 235/462.06, 462.017;
702/104
See application file for complete search history.

(56) References Cited

U.S. PATENT DOCUMENTS

| | | | |
|---|---|---|---|
| 4,479,718 A * | 10/1984 | Alman | 356/405 |
| 4,886,355 A * | 12/1989 | Keane | 356/73 |
| 5,377,000 A | 12/1994 | Berends | |
| 5,401,977 A | 3/1995 | Schwarz | |
| 6,031,620 A * | 2/2000 | Typpo | 356/445 |
| 6,233,053 B1 | 5/2001 | Preston et al. | |
| 2006/0256341 A1* | 11/2006 | Kuwada | 356/445 |
| 2009/0316149 A1 | 12/2009 | Ingleson et al. | |

* cited by examiner

*Primary Examiner* — Anh V La
(74) *Attorney, Agent, or Firm* — Leason Ellis LLP

(57) ABSTRACT

An apparatus and system for providing a solution that enables technicians or other technical professionals obtain both an accurate color value for a sample as well as an accurate gloss value while using a spectrophotometer and an integrated gloss meter device. The present invention allows for accurate color and gloss value analysis of samples using improved compensation values by using a reference sensor to correct the variations in intensity of a light source.

20 Claims, 5 Drawing Sheets

SYSTEM AND APPARATUS FOR GLOSS CORRECTION IN COLOR MEASUREMENTS

FIELD OF THE INVENTION

The present invention relates a system and apparatus for compensating the gloss measurement value of a sample when using a spectrometer with an integrated gloss meter. More particularly the apparatus relates to the operation of integrated spectrophotometers and gloss meters wherein a reference channel of the spectrophotometers provides compensation and calibration data for the gloss meter.

BACKGROUND OF THE INVENTION

Gloss is an important quality criterion for assessing the quality of paints, coatings, plastic surfaces and the like. Measuring gloss with results that are repeatable and precise is, however, exceptionally difficult. In its general definition, gloss is the property of a surface regarding its ability to reflect light. The more complex the shape, the more difficult it is to accurately measure gloss. Adding to the complications, the light used to measure gloss is itself imprecise. The characteristics of light render the intensity of the reflected light subject to variations due to voltage or frequency changes, as well as localized moisture or other atmospheric conditions. The physical dimensions of a sample combined with the inconsistent intensity of the light sources make it difficult to standardize gloss measurements across samples. As well, considerable physical deviations within a sample make it difficult to standardize the results of gloss measurements.

Photo-spectrometers are known and widely used in various technical disciplines. Commonly owned U.S. Published Patent Application No. 2009/031649, which is hereby incorporated by reference, describes a ring shaped spectrophotometer for use in measuring the color of a sample. Spectrophotometers are used for the purposes of measuring and calibrating various sample colors and hues. Similarly, gloss meters are likewise standard components of color sampling and measuring devices. Both of these devices are commonly combined to provide general color and gloss measuring functions. In both devices, light is reflected off the surface and is measured and recorded with optical sensors. Optical sensors have improved fidelity and reliability over human observation; however, the precision of the current art devices is in need of improvement.

Conventional gloss-meters and gloss-measurement devices suffer from a number of inherent drawbacks. Many of these drawbacks are the result of technical limitations due to component selection and orientation of both light sources and sensors. In fact, most of the mechanisms for determining the gloss of an object are quite limited in their mechanical operation.

There are drawbacks when using conventional gloss measuring devices. U.S. Published Patent Application US 2009/0316149 to Ingleson, which is hereby incorporated by reference, provides a spectral measurement device that includes a gloss measurement option. The reference provides for a spectrometer using a 45°/0° or sphere based color measurement instrument, while including a separate 60° gloss measurement channel. This measurement channel is separated from the main spectral measurement devices. Additionally, the gloss measurement device can only be operated while the spectral device is not engaged. Furthermore, Ingleson fails to compensate for the inherent variability in the light source.

U.S. Pat. No. 5,401,977 to Schwarz, which is hereby incorporated by reference, is directed to a manual measurement of a gloss sample designed to achieve a suitable compensation factor. That apparatus and system is not configured to use a reference channel to automatically calibrate the sample using a light channel of a spectrophotometer. Additionally, the Schwarz reference fails to compensate for thermal and other drifts in the light source.

U.S. Pat. No. 5,377,000 to Berends, which is hereby incorporated by reference, is directed to a gloss measurement system that uses signal value compensation to correct for errors in the measurement. The device of Berends is limited to using two light sources at opposite ends of the visible wavelength spectrum.

U.S. Pat. No. 6,233,053 to Preston, herein incorporated by reference, is directed to a dual function gloss measurement device. The device of Preston is limited to using multiple light sources to provide corrected gloss values to a measurement device.

These deficiencies in the prior art render the ability to measure gloss difficult and inconsistent. Therefore, what is needed in the art is an integrated gloss measurement device and spectrophotometer that provides improved gloss measurement results. What is also needed in the art is such a system and apparatus that also simplifies and standardizes gloss measurements. What is further needed is such a system and apparatus that is capable of engaging gloss and color sensors concurrently in determining on a gloss value of a sample.

SUMMARY OF THE INVENTION

In accordance with a broad aspect of the present invention, the apparatus disclosed herein provides for an improved spectrophotometer with an integrated gloss meter that overcomes the deficiencies inherent in the prior art. In more particular aspects, the present invention provides for an integrated spectrophotometer device wherein at least one measurement channel of the spectrophotometer is used to drift-compensate the gloss measurements obtained when using an electric light source, including a light emitting diode (LED). The present invention, in a particular embodiment, provides an integrated gloss measurement apparatus where the color measurement channel is used to compensate for variable intensity of the light source. In another embodiment, light from a gloss meter's light source is introduced directly to the reference channel of a color sensor. Without introducing a separate reference channel to the gloss meter, this embodiment achieves the functionality of a reference channel to normalize out the gloss-meter light fluctuations and measure only the light intensity variations inherent to the color of the sample, Furthermore, an embodiment of the present invention provides an operational mode wherein the reference channel of the spectrophotometer is used to compensate for the light-intensity fluctuations of a variety of gloss meter light source types.

DESCRIPTION OF ILLUSTRATIVE CERTAIN EMBODIMENTS OF THE INVENTION

By way of overview and introduction, the present invention concerns a system and apparatus for the calibration of gloss values when used in an integrated spectrophotometer. The apparatus and system provides a solution that enables technicians or other technical professionals obtain both an accurate color value for a sample as well as an accurate gloss value while using the same device. The present invention allows for accurate color and gloss value analysis of samples using improved compensation values. Furthermore, the present invention allows for the gloss of the sample to be investigated in a manner that does not require the spectrophotometer to be completely disabled. The present invention also provides for an integrated color and gloss meter that relies on fewer components than those provided in the prior art, providing a simpler and less expensive construction.

Figure 1:
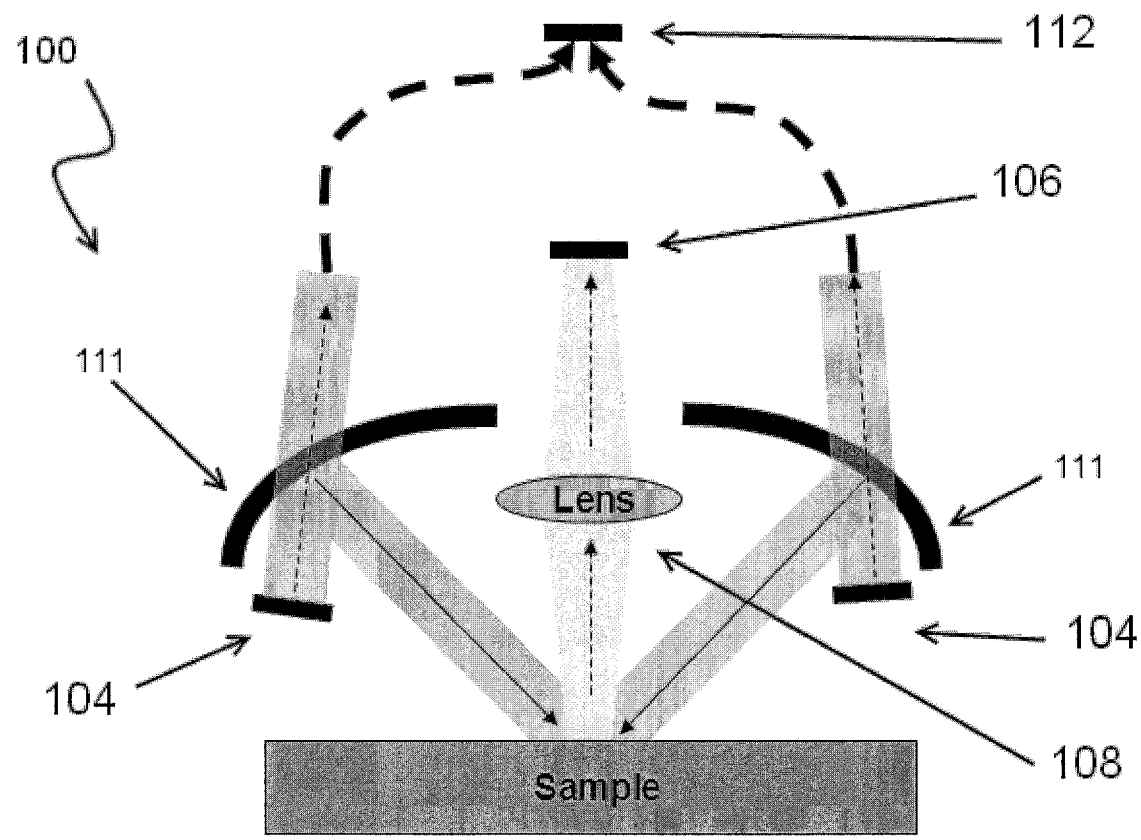
FIG. 1 is a cut-away drawing of an embodiment of the present invention.
Figure 2:
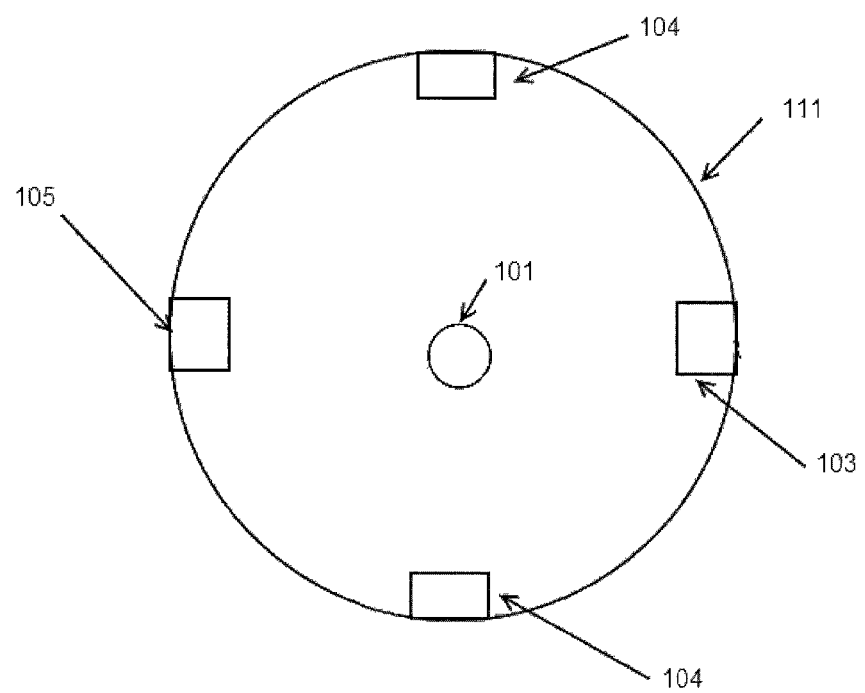
FIG. 2 is a top view of an embodiment of the present invention.

The present invention described in the foregoing figures incorporates two different types of light source found within an integrated spectrophotometer/gloss-meter: the color light source (a light source, possibly spatially distributed, used by the spectrophotometer to measure the spectral reflectance of the sample) shown in FIG. 1, and the gloss light source (a localized light source used by the gloss meter to measure the gloss of the sample), shown in FIG. 2. It will be understood that, at any given time, at most one of these light source varieties will be activated.

Additionally, the device described provides four kinds of optical channel in an integrated spectrophotometer/gloss-meter: (a) The sample color channel collects light from the spectrophotometer light source after the light reflects off the sample; (b) the reference color channel collects light from the spectrophotometer light source that does not interact with the sample; (c) the sample gloss channel collects light from the gloss-meter light source after the light is reflected from the sample; and (d) the reference gloss channel collects light from the gloss-meter light source that does not interact with the sample. In one arrangement, the gloss meter is configured to use the reference color channel as the reference gloss channel. In another arrangement, an additional channel is used as a special reference gloss channel which is configured to collect light from the gloss-meter light source that is reflected from the sample.

The present invention is directed to a device for calibrating and compensation for gloss measurement values that result from measuring the gloss of the surface of an object. Those skilled in the art will appreciate those specimens and products that are suitable for gloss measurement. It is well known in the art to provide a gloss compensation value that is the ratio of the output of a gloss sample channel measurement to the output of a reference channel output. The present invention provides for this compensation value through the use of integrated spectrophotometer reference sensors and gloss sample sensors. Thus, the gloss sensor and associated elements (collectively gloss meter) necessary to provide an accurate gloss measurement are integrated within a single integrated spectrophotometer and gloss meter. However, those skilled in the art will appreciate that the gloss meter elements can be modified to fit a number of design constraints. For example, in a particular embodiment the gloss meter elements are configured as a removable module or modules that are separately attached to a spectrophotometer by cables or conduits.

FIGS. 1 and 2 show an integrated spectrophotometer and gloss meter 100. As shown in FIG. 1, the arrangement illustrated includes a reflective housing in the form of a dome or ring shaped structure 111 secured over a sample 101 to be analyzed. FIG. 1 depicts the spectrophotometer components of the integrated spectrophotometer and gloss meter 100. A plurality of light elements (collectively 104) comprising the spectrophotometer light source are distributed about the perimeter of the dome 111 (only two shown). A sample color sensor 106 and lenses 108 provide a sample spectrophotometer channel for capturing light that has interacted with the sample 101. A second, separate reference channel color sensor 112 is provided for capturing light that has not interacted with the sample 101. The outputs of the reference and sample channels are directed through a fiber optic cable (not shown) to an external light processor or computer configured to analyze the channel data received into a memory thereof and acted upon by a processor configured by code executing therein to perform the analysis. The elements described are assembled from modular components, thus allowing for ease of manufacture. A gloss sensor and the other components performing the gloss meter functions of the present invention are located on the perimeter of the dome 111 and are positioned between the light elements 104 (seen more clearly in FIG. 2) and are thus not visible in FIG. 1. Due to the modular manufacture of the apparatus, the placement of the gloss meter elements along the dome 111 is variable depending on the specific needs of the user or manufacturer.

Figure 3:
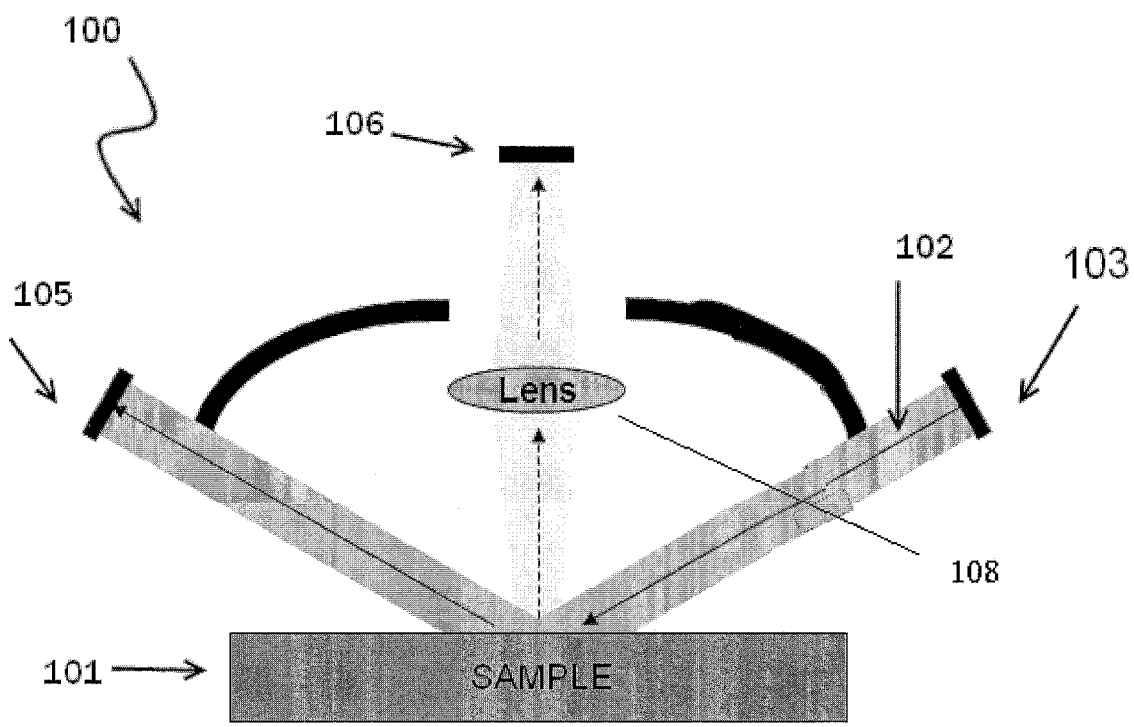
FIG. 3 is an illustrative diagram of the functioning of the device in accordance with one embodiment of the invention.
Figure 4:
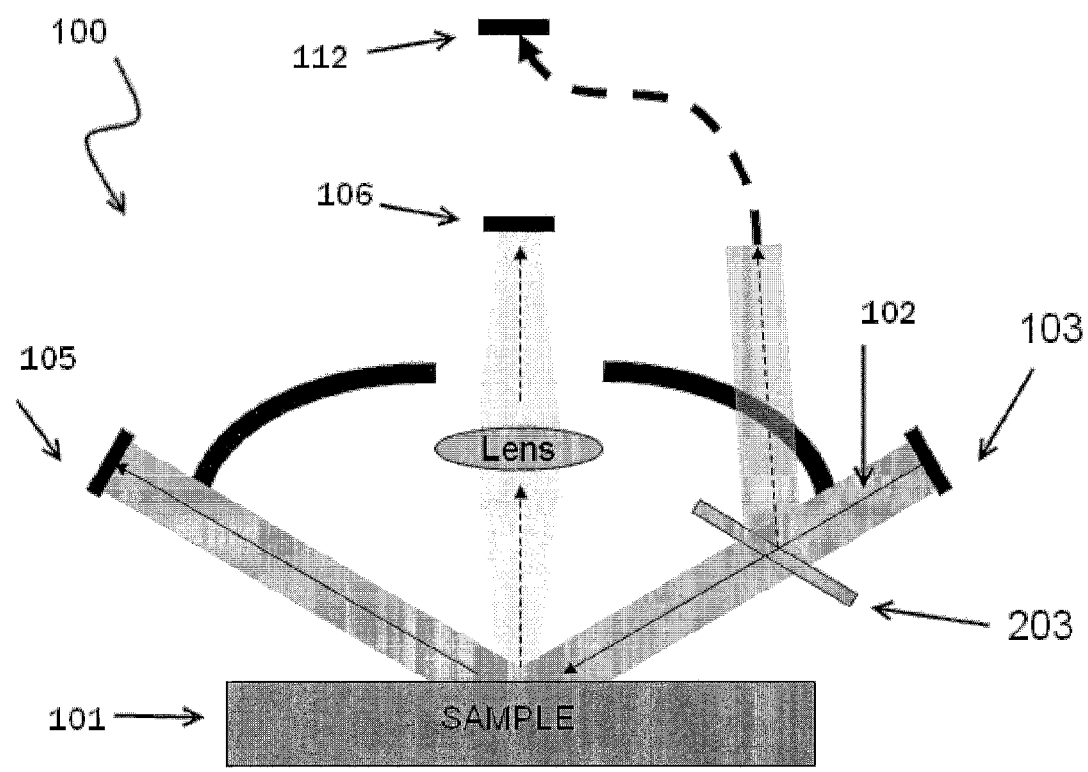
FIG. 4 is an illustrative diagram of an alternative embodiment of the invention.

The curved dashed lines illustrated in FIGS. 1, 3-4 indicate an optical path of the light beam that might be curved. For example, the curved path represents use of a light pipe, fiber optic cable or light bending device. The illustrated arrangement depicts the color channel sensors located in a different planar section than the gloss channels and gloss light sources, (hence the gloss meter components are not visible) because in the illustrated arrangement the color illuminators 104 are in a ring around the central axis and the gloss sensor is only at one azimuthal angle.

FIG. 2 shows an integrated spectrophotometer and gloss meter 100 from a top view. To simplify the drawing, the color sensor 106, lenses 108 and color reference sensor are not visible in this illustration. As depicted, the gloss sensor 105 is located on the periphery of the dome 111 and directed to receive light reflected of the sample 101 from light source 103. The gloss sensor 105 and its corresponding light source 103, which collectively function as a gloss meter, are located between the spectrophotometer light sources 104. The relative positions of the elements described in FIG. 2 are purely for the sake of illustrating the schematic arrangement and do not restrict the range of relative orientations possible for of the elements being described. The optimal arrangement of the elements can be determined in a conventional manner if and when the gloss meter is incorporated into a standard or a custom spectrophotometer.

FIG. 3 provides an alternative view of the integrated spectrophotometer and gloss meter 100, wherein the gloss meter components are visible. The arrangement illustrated provides a light source 103 that is configured to direct light energy at an incident angle to a sample 101. The light source 103 is independent from the light sources incorporated into the spectrophotometer portion of the device 100. In an alternative arrangement, one of the plurality of light sources 104, properly configured, functions as the light source 103. Additionally, the operation of the light source 103 is directed by manual or computer control. In the depicted embodiment, the light source 103 is a single LED (light emitting diode). In an alternative arrangement the LED light source 103 comprises a plurality of lighting elements selected for use in view of their respective ranges of emission wavelength and intensity characteristics. In the alternative, the gloss light source 103 is a tungsten lighting element or a narrow-band or monochromatic light beam, including laser light. The light source 103 is configured to emit a light beam 102 in the visible or invisible spectrum. The emitted light beam 102 travels to the sample 101 and is reflected at an angle that allows the reflected light beam 102 to travel to a suitably positioned gloss sensor 105. Regardless of the type of light source used, the resulting light beam lacks uniform intensity over time. This variation in intensity can be the result of numerous factors like thermal drift, voltage fluctuation, current fluctuation, mechanical movement and air pressure differentials, but the sample is expected to be stable in time. It is this highly variable light beam that is captured by the gloss sensor 105.

The gloss sensor 105 is an industry standard gloss sensor configured to measure specular reflection of the incident light on the surface of the sample 101, The gloss sensor 105, upon capturing variable intensity light incident off the sample 101, outputs the light as a sample channel value. The sample channel value is derived from light that has interacted with the sample, and hence contains information about the sample and the light source. The sample channel output is then directed to a light measuring device or computer 305 (see FIG. 5) that is separate from or integrated into the spectrophotometer. In the depicted embodiment, the output is accomplished via fiber optic cables (not shown). In an alternative arrangement, electro-optical cables, electrical conduits or RF conversion devices are employed to output the reference channel to the light measuring device 305. In an alternative embodiment, the light measuring device converts the reference channel into a measured gloss sensitive value for storage in a storage medium or for display on a display device.

The position of the gloss sensor 105 within the housing of the spectrophotometer is such that it is able to receive sufficient incident light reflected from the sample. For example, the gloss sensor 105 is angled at 60° from the surface of the specimen 101. Alternative angles for the gloss meter can be established in alternative arrangements.

The embodiment of FIG. 3 also provides an independent spectrophotometer sample color sensor 106. The sample color sensor 106 is an industry standard sensor designed to accurately measure color values. The sample color sensor 106 provides a reference channel that is operational concurrently while the gloss meter function is activated. The sample color sensor 106 is positioned so that a portion of the incident light from the gloss light source 103 is reflected off the specimen 101 and reaches the spectrophotometer sensor 106. In an alternative arrangement, a lens 108 is positioned between the specimen 101 and functions to focus the incident light upon the color sensor 106. Upon capture of the reflected light beam 102, the sample color sensor 106 generates a reference channel signal readable by an external or integrated light measuring device or computer 305. In this configuration, the reference channel is comprised of light that has interacted with the sample, referred to herein as a measured color-sensitive value.

In an alternative embodiment, as shown in FIG. 4, the sample 101 is not used to assist in compensation of the gloss measurement. In this embodiment, the gloss light source 103 directs the light beam 102 towards a light division device 203. In the illustrated arrangement, the light division device 203 is a beam splitter configured to direct light in at least two different directions relative to the incoming beam 102. Those skilled in the art will appreciate the specific mode of operation and construction of the light division device 203. For example, in the illustrated arrangement the light division device 203 is an intensity beam splitter. In alternative arrangement, the light division device 203 is a wavelength beam splitter, which passes some wavelengths while reflecting others, or a spatial beam splitter, which passes the central waist of the light beam through an optically transparent center region while reflecting the remainder of the beam.

The light division device 203 directs a portion of the light beams 102 to the sample 101 and a portion to the sample color reference sensor 106. The color reference sensor 112, upon capture of the light from light division device 203, generates a reference channel signal that is comprised of information regarding the variable intensity of the light source and has no sample color information. The reference channel information is then output to a light sensing device or computer 305 where it is compared to the sample channel generated by the gloss sensor 105. Through this comparison, made by a processor executing code, the variations inherent in the gloss light source 103 are then compensated to produce a more accurate measurement of the gloss value of the specimen.

In an alternative arrangement of the elements illustrated in FIGS. 3 and 4, the gloss measurement system employs the use of both the color measurement channel 106 and the color reference channel 112. This arrangement provides that once the light beam is incident on the sample, it is captured by both a color measurement sensor 106 and the gloss sensor 105. Additionally, the light division device 203 is used to direct a portion of the light beam 103 to the color reference sensor 112. Through this arrangement, the three separate information channels are used to generate a more accurate compensation metric for the gloss measurement.

In a further arrangement of elements, the gloss reference channel is a gloss specific reference sensor, and is a separate and distinct device from the reference color sensor 112.

Figure 5:
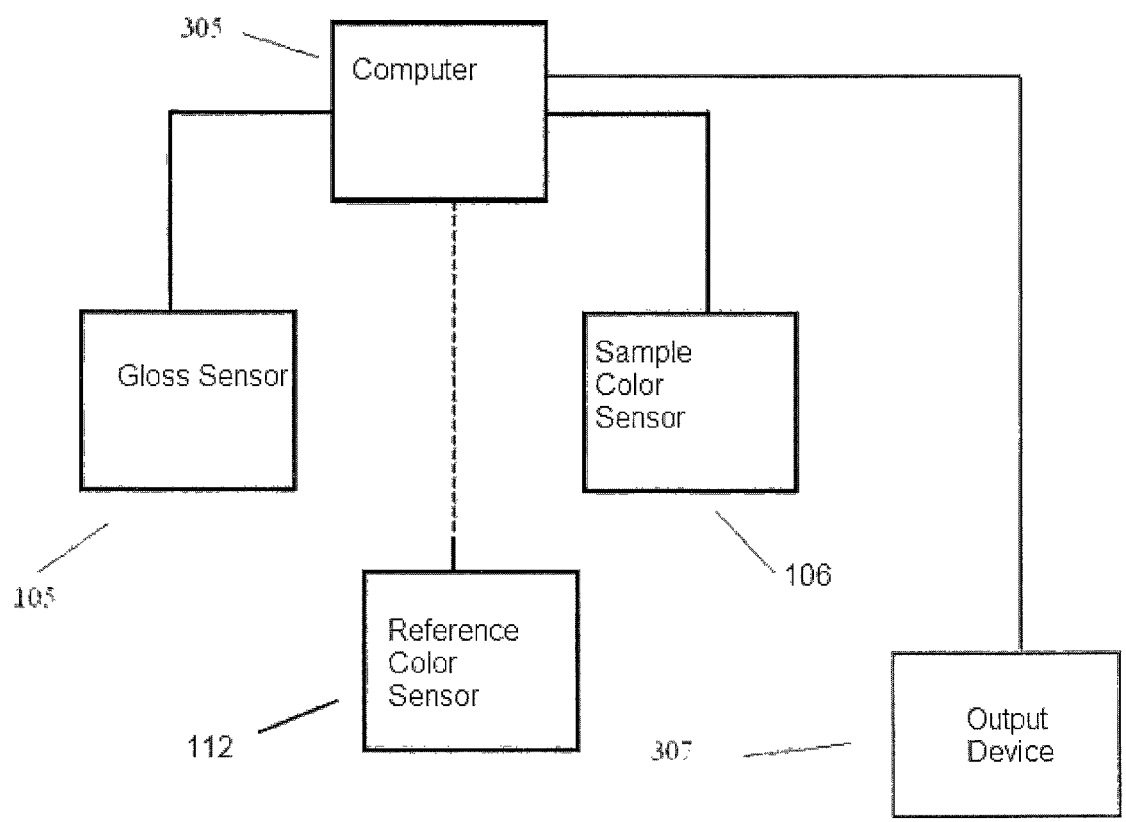
FIG. 5 is a schematic diagram of an embodiment of the invention.

As shown in FIG. 5, when the gloss light source 103 is activated, a light beam 102 is directed to the sample 101. Of this light beam 102, a portion is reflected to the gloss sensor 105, and a portion is directed to the color sensor 106. When the light beam 102 is incident upon the color sensor 106 a color channel signal is generated and is output to a light measuring device or a computer 305 equipped to measure light values. This reference channel signal is related to the color of the sample and the specific characteristics of the gloss light source 103. Additionally, the optional reference color channel 112, when struck by light from the light source 103, will also output to the measuring device or processor 305. The light measuring device or processor 305 is configured to compare known color signal information from the sample and the reference channel signal generated by the color sensor 106 during the gloss measurement operation. The computer is equipped with sufficient memory and storage to perform analysis on the reference channel and sample channel.

In the embodiment depicted in FIG. 3, the known color signal information is derived from measuring the sample with the standard spectrophotometer and obtaining an output (i.e., from a sample channel of the spectrophotometer). In the alternative embodiment depicted in FIG. 4, the reference channel generated by color sensor 106 is solely due to the light source, Therefore, the values of the raw gloss data generated by the sample channel is compensated and modified by the light source data generated by the reference channel. The computer 305 uses the light information supplied by the reference and sample channels to compensate for the variations inherent in light sources due to thermal drift and other light source variations.

The gloss light source 103 has inherent variations that can alter the precision of the gloss measurement. For example, because LED light is thermally superior to traditional lighting elements (e.g. tungsten), thermal drift is left uncompensated in standard gloss measurements. This thermal drift leads to imprecise measurements of gloss values, especially when the device is used in an intensive manner. However, thermal drift is not the only source of variation that can occur. Electrical current fluctuations as well as atmospheric conditions can alter the intensity. In the present embodiment the color reference channel and color sample channel, once controlled for color information, is used to compensate the gloss measurement sample channel generated by the gloss sensor 105. The computer 305 compares the sample channel and the reference channel signals in order to compensate for LED fluctuations in real time. The corrected value can then be displayed on an output device 307. Alternatively, the computer 305 is configured to store the values of the compensated measurement and uncompensated measurement for later statistical or analytical investigation in a database. In a further alternative embodiment, the computer 305 is configured to trigger an alarm when the compensation value reaches a certain threshold. In a further embodiment the trigger is a signal generated from the computer that is related to the value of the ratio of the sample channel value to reference channel value.

The computer 305 processes the information from the sensors to determine gloss values using widely understood algorithms. For instance, the computer 305 is equipped to perform and analyze the color and gloss measurements. For example, the computer 305 can be equipped to perform super-ellipsoid measurements, least square fit optimizations, and/or similar computational analysis on the signal channel data. The fiber optic conduits of the depicted elements, the fiber optic units are configured to transmit 1 or more data channels to the computer 305, thereby providing a secure link without additional optical interference. For example, the gloss sensors described herein are equipped to output each channel on a different modulated frequency. Those skilled in the art will appreciate the various computational mechanisms available to computer 305 for obtaining a corrected gloss value from a data channel inputs.

The present invention also incorporates a methodology of using the apparatus to carry out and achieve the function of compensating a gloss measurement by adopting a reference channel of a spectrophotometer as a reference channel for the gloss meter. Such a method involves, but is not limited to, a positioning step, wherein the object or sample to be analyzed is positioned under a spectrophotometer. A measuring step is provided, wherein the gloss meter obtains a raw gloss data value of the specimen. A compensation step is provided wherein the spectrophotometer senor provides a reference channel for the gloss meter. A comparison step is provided wherein the gloss reference channel data and the gloss sample data are compared so as to remove variations due to the specific light element. An output step provides a compensated gloss value in an electronic format ready for storage or transmittal to a display device. The above processing functions can be operating as a series of programmed steps preformed by a properly configured computer system using one or more modules of computer-executable code. For instance, a set of software modules can be configured to cooperate with one another to configure a processor when executed they provide accurate gloss measurement information to a display device as described herein. In this regard, there can be a measuring module, a compensation module, a comparison module, and an output module.

The measuring module can be configured as a series of discrete sub-modules designed to access data from a gloss meter sensor such as the sensor described in connection with FIGS. 3-4. The measuring module incorporates functions enabling the present apparatus to receive gloss information from light that is incident upon a specimen.

A compensation module can be configured as a series of discrete sub-modules designed to access one or more reference or sample channels of the color sensor and provide an output representing only the gloss light data and not the color data of the specimen. Adopting the sample color channel as the special gloss reference channel (in the sense of (e) above) will ensure stability of the gloss measurement, but will not provide an absolute scale of reflection; adopting the color reference channel as the gloss reference channel does provide an absolute scale, and hence is preferable.

The comparison module can be configured as a series of discrete sub-modules providing the present invention with the necessary functionality to compare the gloss measurement value with the values obtained from the compensation module. In an embodiment of the present invention, statistical analysis of the reference channel is preformed to identify key data points. These key data points are used to indicate variations on intensity that are due solely to the light source and not to physical conditions of the product.

The output module can be configured as a series of discrete sub-modules designed to provide functionality to the present invention. The discrete sub-modules can include instructions for combining the compensated gloss value and formatting the value for display on a particular display device or for updating a database of reference values and stored values.

Each of these modules can comprise hardware, code executing in a processor, or both, that configures a machine such as the computing system to implement the functionality described herein. The functionality of these modules can be combined or further separated, as understood by persons of ordinary skill in the art, in analogous implementations of embodiments of the invention.

It should be understood that various combination, alternatives and modifications of the present invention could be devised by those skilled in the art. The present invention is intended to embrace all such alternatives, modifications and variances that fall within the scope of the appended claims.

While the invention has been particularly shown and described with reference to a preferred embodiment thereof, it will be understood by those skilled in the art that various changes in form and details may be made therein without departing from the spirit and scope of the invention.

We claim:

1. An apparatus for compensating the gloss measurement value of a gloss meter comprising:
   an activated light source having a light output, configured to project light in the direction of a sample having a gloss characteristic to be measured, wherein at least one characteristic of the output changes over time;
   at least one gloss-sensitive sensor positioned as a sample channel so as to receive light reflected from the sample and output a measured gloss-sensitive value;
   at least one color-sensitive sensor positioned as a gloss reference channel so as to receive light reflected from the sample and output a measured gloss-sensitive value; and
   a processor configured to compare the outputs from the sample channel to the gloss reference channel and generate a calibrated gloss measurement value that is substantially free of variations of the activated light source, wherein the processor is further configured to output the calibrated gloss measurement value.

2. The apparatus for compensating gloss measurement value of claim 1, wherein a secondary reference gloss channel is configured to collect light from the gloss-meter light source that is reflected from the sample.

3. The apparatus for compensating gloss measurement value of claim 1, wherein the processor is further configured to connect to an alarm and a database, wherein the alarm is activated by a trigger signal generated by the processor.

4. The apparatus for compensating gloss measurement value of claim 3, wherein the database is configured to store a range of gloss measurement reference values.

5. The apparatus for compensating gloss measurement value of claim 4, wherein the processor is further configured to compare the stored reference value range with the calibrated gloss measurement value and generate the trigger signal to activate the alarm when the calibrated gloss measurement value is outside of the range.

6. The apparatus for compensating gloss measurement value of claim 1, wherein the gloss reference channel sensor is a color reference sensor of a spectrophotometer.

7. An apparatus for compensating the gloss measurement value of a gloss meter comprising:
    an activated light source, configured to project light in the direction of a sample having a gloss characteristic to be measured, wherein there are variations in the intensity of the light source over time;
    at least one gloss-sensitive sensor positioned as a sample channel so as to receive light reflected from the sample and output a measured gloss-sensitive value;
    at least one color-sensitive sensor positioned as a gloss reference channel so as to receive light reflected from a light division device prior to contact with the sample and output a measured color-sensitive value; and
    a processor configured to compare the outputs from the sample channel to the gloss reference channel and generate a calibrated gloss measurement value that is substantially free of variations of the activated light source, wherein the processor is further configured to output the calibrated gloss measurement value.

8. The apparatus for compensating gloss measurement value of claim 7, wherein a secondary reference gloss channel is configured to collect light from the gloss-meter light source that is reflected from the sample.

9. The apparatus for compensating gloss measurement value of claim 8, wherein the processor is further configured to connect to an alarm and a database, wherein the alarm is activated by a trigger signal generated by the processor.

10. The apparatus for compensating the gloss measurement value of claim 9, wherein the database is configured to store a range of reference value gloss measurements.

11. The apparatus for compensating gloss measurement value of claim 10, wherein the processor is further configured to compare the stored reference value range with the calibrated gloss measurement value and generate the trigger signal to activate the alarm when the calibrated gloss measurement value is outside of the range.

12. The apparatus for compensating gloss measurement value of claim 11, a color sensitive reference channel sensor is used in addition to the gloss-sensitive and color sensitive sensors.

13. The apparatus for compensating gloss measurement value of claim 7, wherein the light division device comprises a light intensity beam splitter.

14. The apparatus for compensating gloss measurement value of claim 7, wherein the light division device comprises a spatial beam splitter.

15. The apparatus for compensating gloss measurement value of claim 7, wherein the light division device comprises a wavelength beam splitter.

16. The apparatus for compensating gloss measurement value of claim 7, wherein the gloss reference channel sensor is a color reference sensor of a spectrophotometer.

17. A computer-implemented method for utilizing a particular connection with an electronic device in compensating the measurement of a gloss characteristics of a sample using a gloss meter, the particular electronic device having a processor, a memory, an input device, an output device and a compensation application stored in the memory and executable by the processor, the method comprising:
    projecting light onto a sample to be measured, the light having at least one characteristic that varies over time;
    generating a sample channel value from a gloss sensor related to the amount of gloss possessed by the sample;
    generating a gloss reference channel value from a color sensor wherein the gloss reference channel value is related to the variation in the light projected onto the sample;
    comparing the sample channel value with the gloss reference channel value using the processor by executing the compensation application so as to identify a component of the sample channel value due to intensity variations;
    generating a calibrated gloss measurement value based on the comparison of the sample channel value with the gloss reference channel value;
    comparing the calibrated gloss measurement values to a reference gloss value range stored in the electronic device memory; and
    outputting a signal when the gloss measurement value is outside the reference gloss range.

18. The method according to claim 17, further comprising the step of:
    triggering a human perceptible alarm when the output signal is generated, wherein the alarm has an audio, visual, or a combination of both audio-visual characteristics.

19. The method according to claim 18, further comprising the step of:
    generating a plurality of gloss reference channel values from a plurality of color sensors wherein the gloss reference channel value is related to the variation in the light projected onto the sample.

20. A computer-implemented method for utilizing a particular connection with an electronic device in compensating the measurement of a gloss characteristics of a sample using a gloss meter, the particular electronic device having a processor, a memory, an input device, an output device and a compensation application stored in the memory and executable by the processor, the method comprising:
    projecting light onto a sample to be measured, the light having at least one characteristic that varies over time;
    from a sample channel, generating a sample channel value from a gloss sensor related to the amount of gloss possessed by the sample;
    monitoring variation in the at least one characteristic of the light using a color sensor arranged to pick up the light from (a) the sample channel, or (b) a gloss reference channel in which the light is projected onto the sample, or (c) both the sample channel and the gloss reference channel;
    executing the compensation application on the monitored variation so as to identify a component value due to intensity variations;
    generating a calibrated gloss measurement value based on the identified component value;
    comparing the calibrated gloss measurement values to a reference gloss value range stored in the electronic device memory; and outputting a signal when the gloss measurement value is outside the reference gloss range.

* * * * *